(12) United States Patent
Castelli et al.

(10) Patent No.: US 7,355,078 B2
(45) Date of Patent: Apr. 8, 2008

(54) PROCESSES FOR THE PREPARATION OF TOMOXETINE

(75) Inventors: Eugenio Castelli, Arlate di Calco (IT); Giuseppe Lo Monaco, Seregno (IT); Silvia Mantovani, Cesano Maderno (IT); Paola Daverio, Villasanta (IT); Paolo Riva, Monza (IT); Alessandra Vailati, Seregno (IT); Stefano Bianchi, Como (IT)

(73) Assignee: Teva Pharmaceutical Fine Chemicals S.r.l., Bulciago (LC) (IT)

( * ) Notice: Subject to any disclaimer, the term of this patent is extended or adjusted under 35 U.S.C. 154(b) by 194 days.

(21) Appl. No.: 11/170,429

(22) Filed: Jun. 28, 2005

(65) Prior Publication Data

US 2006/0009531 A1    Jan. 12, 2006

Related U.S. Application Data

(60) Provisional application No. 60/690,738, filed on Jun. 14, 2005, provisional application No. 60/689,778, filed on Jun. 9, 2005, provisional application No. 60/675,369, filed on Apr. 26, 2005, provisional application No. 60/666,666, filed on Mar. 30, 2005, provisional application No. 60/652,330, filed on Feb. 11, 2005, provisional application No. 60/652,332, filed on Feb. 11, 2005, provisional application No. 60/652,331, filed on Feb. 11, 2005, provisional application No. 60/622,065, filed on Oct. 25, 2004, provisional application No. 60/609,716, filed on Sep. 14, 2004, provisional application No. 60/583,641, filed on Jun. 28, 2004, provisional application No. 60/583,644, filed on Jun. 28, 2004, provisional application No. 60/583,643, filed on Jun. 28, 2004.

(51) Int. Cl.
*C07C 213/08* (2006.01)
(52) U.S. Cl. .................................... 564/353
(58) Field of Classification Search ............... None
See application file for complete search history.

(56) References Cited

U.S. PATENT DOCUMENTS 4,018,895 A    4/1977    Molloy et al.

| 4,777,291 A | 10/1988 | Misner |
| 4,868,344 A | 9/1989 | Brown |
| 5,658,590 A | 8/1997 | Heillgenstein et al. |
| 6,333,198 B1 | 12/2001 | Edmeades et al. |
| 6,541,668 B1 | 4/2003 | Kjell et al. |

FOREIGN PATENT DOCUMENTS

| DE | 41 23 253 A1 | 1/1993 |
| EP | 0 052 492 A1 | 5/1982 |
| EP | 0 193 405 A1 | 9/1986 |
| EP | 0 721 777 A2 | 1/1995 |
| WO | WO 94/00416 | 1/1994 |
| WO | WO 00/58262 | 10/2000 |
| WO | WO 00/64855 | 11/2000 |
| WO | WO 2006/004923 A2 | 1/2006 |
| WO | WO 2006/004976 A2 | 1/2006 |
| WO | WO 2006/004977 A2 | 1/2006 |
| WO | WO 2006/004979 A2 | 1/2006 |
| WO | WO 2006/020348 A2 | 2/2006 |

OTHER PUBLICATIONS

Srebnik, M. et al. "Chiral Synthesis via Organoboranes. 18. Selective Reductions. 43. Dissopinocampheylchloroborane as an Excellent . . . " J. Org. Chem. (1988), vol. 53, p. 2916-2920.
Anon (R)-(-)-N-Methyl-3-(2-Methylphenoxy)Phenyl-3-Phenylpropylamine (S)-(+)-Mandelate Chemical Abstracts Service XP-002367858 Dec. 29, 2004.
Koenig, T.M. et al. "A Convenient Method for Preparing Enantiomerically Pure Norfluoxetine, Fluoxetine and Tomoxetine" Tetrahedron Letters, vol. 35, No. 9, pp. 1339-1342 (1994).
Strobel, H.A.; Heineman, W.R., Chemical Instrumentation: A Systematic Approach, 3rd dd. (Wiley & Sons: New York 1989)—pp. 391-393, 879-894, 922-925, 953.
Snyder, L.R.; Kirkland, J.J., Introduction to Modem Liquid Chromatography, 2nd ed. (John Wiley & Sons: New York 1979)—p. 549-552, 571-572.
Sellers, J.A. et al. "Determination of the Enantiomer and Positional Isomer Impurities in Atomoxetine Hydrochloride with Liquid Chromatography Using Polysaccharide Chiral Stationary Phases." *J. of Pharmaceutical and Biomedical Analysis*, vol. 41, pp. 1088-1094 (2006).

*Primary Examiner*—Brian Davis
(74) *Attorney, Agent, or Firm*—Kenyon & Kenyon LLP

(57) ABSTRACT

Provided are processes for preparing tomoxetine comprising reacting N-methyl-3-hydroxy-3-phenylpropylamine with dimethylsulfoxide (DMSO) and 2-fluorotoluene in the presence of an alkali base to form tomoxetine. Also provided is the conversion of said tomoxetine into atomoxetine or a pharmaceutically acceptable salt thereof.

17 Claims, No Drawings

PROCESSES FOR THE PREPARATION OF TOMOXETINE

CROSS-REFERENCE TO RELATED APPLICATIONS

This application claims the benefits of U.S. Provisional Patent Application Nos. 60/583,641, filed Jun. 28, 2004, 60/609,716, filed Sep. 14, 2004, 60/622,065, filed Oct. 25, 2004, 60/652,330, filed Feb. 11, 2005, 60/583,644, filed Jun. 28, 2004, 60/652,332 filed Feb. 11, 2005, 60/583,643, filed Jun. 28, 2004, 60/652,331, filed Feb. 11, 2005, 60/666,666, filed Mar. 30, 2005, 60/675,369, filed Apr. 26, 2005, 60/689,778, filed Jun. 9, 2005, and 60/690,738, filed Jun. 14, 2005, the contents of all of which are incorporated herein by reference.

FIELD OF THE INVENTION

The present invention relates to new processes for preparing racemic tomoxetine.

BACKGROUND OF THE INVENTION

Atomoxetine, known as (R)(−)-N-methyl-3-(2-methylphenoxy)-3-phenylpropylamine, has the following structure:

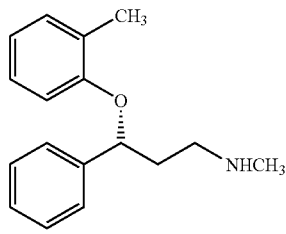

Atomoxetine HCl (STRATTERA®) was originally developed as an antidepressant. It is currently marketed for the treatment of Attention-Deficit/Hyperactivity Disorder (ADHD). Atomoxetine, the (R)-(−) enantiomer of tomoxetine, is an aryloxyphenylpropylamine (e.g., fluoxetine and nisoxetine). It is a competitive inhibitor of norepinephrine uptake in synaptosomes of rat hypothalamus and is approximately 2 and 9 times, respectively, more effective than the racemic mixture and the (+)-enantiomer. See for example: U.S. Pat. No. 4,018,895 (Eli Lilly and Co.), EP 0 052 492 (Eli Lilly and Co.), and EP 0 721 777 (Eli Lilly and Co.).

Several routes of synthesis for 3-aryloxy-3-phenylpropylamines are known in the art. For example, U.S. Pat. No. 4,018,895 by Eli Lilly and Co. discloses an aliphatic nucleophilic displacement of N-protected-3-halogen-3-phenylpropylamines by phenols, followed by N-deprotection. U.S. Pat. No. 4,868,344 by Aldrich-Boranes Inc. relates to the Mitsunobu reaction between 3-hydroxy-3-phenylpropylhalides and phenols, followed by amination of the resulting 3-aryloxy-3-phenylpropylhalides. Unfortunately, the synthetic routes disclosed in these patents require several steps and are burdened by the use of hazardous chemicals, such as diethylazadicarboxylate, triphenylphosphine and thionyl chloride.

U.S. Pat. No. 6,541,668, and WO 00/58262 by Eli Lilly and Co. as well as WO 94/00416 by Richter Gedeon Vegyeszeti Gyar RT disclose an aromatic nucleophilic displacement of an aryl halide by 3-hydroxy-3-phenylpropylamines under strongly basic conditions. The nucleophilic aromatic displacement process disclosed in WO 00/58262 involves reacting N-methyl-3-hydroxy-3-phenylpropylamine with a protected 2-fluorobenzaldehyde, which eventually leads, after functional group interconversion steps, to tomoxetine. The main drawbacks of this process are the additional steps required and the high cost of 2-fluorobenzaldehyde.

U.S. Pat. No. 6,541,668 discloses aromatic nucleophilic displacement conditions in the synthesis of tomoxetine: 1,3-dimethyl-2-imidazolidinone or N-methylpyrrolidinone are used as solvents, starting from N-methyl-3-hydroxy-3-phenylpropylamine and 2-fluorotoluene, under strongly basic conditions (disclosed bases are alkali metal hydrides or alkoxides), at temperatures of less than about 140° C. (yields data are not reported). As pointed out by the '668 patent, aromatic nucleophilic displacement giving tomoxetine cannot be carried out in conditions already known for other 3-aryloxy-3-phenylpropylamines, since 2-fluorotoluene is less activated than other aromatic rings used.

Tomoxetine is an intermediate in the preparation of atomoxetine HCl.

A modest tomoxetine chemical yield with dimethylsulfoxide as a solvent was also reported in Koenig & Mitchell, Tetrahedron Letters, Vol. 35, n. 9, pp. 1339-1342 (1994). The base used is sodium hydride, a more reactive base than alkali metal hydroxides.

Other compounds, such as fluoxetine, can be synthesized through an aromatic nucleophilic displacement process, such as the one disclosed in WO 94/00416.

As indicated by the disadvantages of the methods described in the related art, there is a need in the art therefore for additional processes for preparing tomoxetine in higher yields and shorter reaction times.

SUMMARY OF THE INVENTION

The present invention provides a process for the preparation of tomoxetine utilizing N-methyl-3-hydroxy-3-phenylpropylamine as a starting material, which is reacted with dimethylsulfoxide (DMSO) and 2-fluorotoluene in the presence of an alkali base.

One aspect of the present invention is directed towards a process for the preparation of tomoxetine ((±) N-methyl-3-(2-methylphenoxy)-3-phenylpropalamine) comprising the steps of:

(a) combining N-methyl-3-hydroxy-3-phenylpropylamine with dimethylsulfoxide in the presence of an alkali metal hydroxide to form a slurry;

(b) adding 2-fluorotoluene to the slurry to obtain a reaction mixture;

(c) heating the resultant mixture to obtain tomoxetine; and (d) recovering the formed tomoxetine.

Preferably, the resultant slurry in step (a) is heated prior to the addition of 2-fluorotoluene in step (b), to a temperature of at least 20° C. More preferably, the slurry is heated to a temperature form about 80° C. to about 110° C.

In a preferred embodiment, the resultant mixture in step (c) is heated to a temperature of about 80° C. to about 145° C. Preferably, when the amount of the alkali metal hydroxide added in step (a) is about 3 mole equivalents per mole equivalent of N-methyl-3-hydroxy-3-phenylpropylamine, the resultant mixture is heated to a temperature of about 135° C. to about 145° C. Preferably, when the amount of the alkali metal hydroxide added in step (a) is about 5 mole equivalents per mole equivalent of N-methyl-3-hydroxy-3-phenyl-propylamine, the resultant mixture is heated to a temperature of about 80° C. to 100° C.

Another aspect of the present invention is directed to a process for preparing atomoxetine or a pharmaceutically acceptable salt thereof, comprising a step of preparing tomoxetine by the process described above.

Preferably, the pharmaceutically acceptable salt is atomoxetine hydrochloride

DETAILED DESCRIPTION OF THE INVENTION

As used herein, "room temperature" is meant to indicate a temperature of about 18-25° C., preferably about 20-22° C.

As used herein the term "aromatic solvent" refers to a $C_{6-10}$ aromatic hydrocarbon such as but not limited to benzene, xylene, or toluene.

The present invention provides a process for the preparation of tomoxetine that improves reaction yields and/or shortens the total reaction time. This process comprises the steps of:
(a) combining N-methyl-3-hydroxy-3-phenylpropylamine with dimethylsulfoxide (DMSO) in the presence of an alkali metal hydroxide to form a slurry;
(b) adding 2-fluorotoluene to the slurry to obtain a reaction mixture;
(c) heating the resultant mixture to obtain tomoxetine; and
(d) recovering the formed tomoxetine.

DMSO is used as a reagent and not as a solvent, thus it may be added in small amounts, and may be even considered a catalyst. The amount of DMSO used in the reaction is about 0.1 to about 20 moles per mole of N-methyl-3-hydroxy-3-phenylpropylamine. Preferably, DMSO is added in an amount of about 3 moles to about 4 moles per mole of N-methyl-3-hydroxy-3-phenylpropylamine.

Suitable alkali metal hydroxides may be selected from the group consisting of potassium hydroxide, barium hydroxide and sodium hydroxide. Preferably, the alkali metal hydroxide is potassium hydroxide.

The alkali metal hydroxide in this process is used instead of tert-butoxide, which is used by Eli Lilly in U.S. Pat. No. 6,541,668, and is a much more flammable, air sensitive and expensive reagent. The process of the present invention also avoids the use of sodium hydride, a costly and reactive base that produces tomoxetine in low yields. See for example Koenig & Mitchell, Tetrahedron Letters, Vol. 35, n. 9, pp. 1339-1342 (1994).The Applicants have found that the use of a strong base instead of sodium hydride and tert-butoxide, unexpectedly results in markedly improved yields and preferably in shorter reaction times.

Preferably, the resultant slurry in step (a) is heated prior to the addition of 2-fluorotoluene to a temperature of at least 20° C. Preferably, the slurry is heated to a temperature form about 80° C. to 110° C.

Preferably, 2-fluorotoluene is added to the slurry in an amount of at least about 2 molar equivalents per molar equivalent of N-methyl-3-hydroxy-3-phenylpropylamine.

Optionally, the slurry may be concentrated to remove water, prior to the addition of 2-fluorotoluene. The distillation is preferably conducted by vacuum distillation, at a pressure of less than about 100 mm Hg.

In a preferred embodiment, the resultant mixture in step (c) is heated to a temperature of about 80° C. to about 145° C. Preferably, when the amount of the alkali metal hydroxide added in step (a) is about 3 mole equivalents per mole equivalent of N-methyl-3-hydroxy-3-phenylpropylamine, the resultant mixture is heated to a temperature from about 135° C. to about 145° C. Preferably, when the amount of the alkali metal hydroxide added in step (a) is about 5 mole equivalents per mole equivalent of N-methyl-3-hydroxy-3-phenylpropylamine, the resultant mixture is heated to a temperature of about 80° C. to about 100° C.

Recovering tomoxetine from the reaction mixture can be performed by adding water and an organic solvent to obtain a two-phase system, followed by extraction of tomoxetine with the organic solvent. Preferably, the organic solvent is selected from the group consisting of aliphatic and aromatic hydrocarbons, esters and ethers. More preferably, the organic solvent is selected from the group consisting of toluene, 2-fluorotoluene, benzene, xylenes, di-isopropyl ether, methyl-tert-butyl ether, ethyl acetate n-butylacetate, and isobutylacetate. The preferred organic solvent is toluene or 2-fluorotoluene.

Tomoxetine prepared by the processes of the present invention is obtained in high yield, and preferably, in less than about 4 hours. This process also avoids the use of toxic amidic solvents, such as 1,3-dimethyl-2-imidazolidinone or N-methylpyrrolidinone as disclosed in U.S. Pat. No. 6,541,668.

The present invention further provides processes for preparing atomoxetine and/or a pharmaceutically acceptable salt thereof which include the processes for preparing tomoxetine described herein-above. A preferred pharmaceutically acceptable salt is atomoxetine hydrochloride.

Atomoxetine hydrochloride may be prepared first by an optical resolution of the obtained tomoxetine racemate to yield (R)-(−)-tomoxetine (S)-(+)-mandelate, then adding a base to a mixture of (R)-(−)-tomoxetine (S)-(+)-mandelate and an organic solvent, followed by adding HCl, to obtain atomoxetine HCl.

Moreover, the present invention provides a process for preparing a pharmaceutical composition comprising atomoxetine or a pharmaceutically acceptable salt thereof, which comprises bringing the obtained atomoxetine or a pharmaceutically acceptable salt thereof into contact with one or more pharmaceutically acceptable carriers or excipients.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

HPLC analysis

Instrument: HPLC Hewlett Packard VWD detector HP1100.

Column: YMC ODS-AQ 250 mm×4.6 mm (i.d.) cod. AQ-303

Mobile phase: $NaH_2PO_4$ 0.02M pH 3

Buffer: acetonitrile gradient

Flow: 1.5 ml/min

Temperature: 40° C.

Wavelength: 215 nm

Example 1

Preparation of Tomoxetine 30 g (0.384 mol) of dimethylsulfoxide, 20 g (0.121 mol) of N-methyl-3-hydroxy-3-phenylpropylamine and 22.6 g (0.363 mol) of potassium hydroxide (bulk industrial grade, 90.1% assay) were mixed while stirred and heated at 100° C. for one hour. The resulting slurry was allowed to cool to 80° C., and 40.0 g (0.363 mol) of 2-fluorotoluene was added. The mixture was heated to reflux (135° C.-137° C.) for three hours and allowed to cool to about 90° C. 120 ml of water and 120 ml of toluene were then added. The mixture was stirred for several minutes, and the phases were separated. The aqueous phase was extracted with 3×30 ml of toluene. The organic phases were collected and washed with 3×30 ml of water. Final organic phase weight: 206 g. Tomoxetine content: 14.28% by weight (HPLC assay). Yield: 95.2%.

Example 2

Preparation of Tomoxetine 110 g (1.41 mol) of dimethylsulfoxide, 20 g (0.121 mol) of N-methyl-3-hydroxy-3-phenylpropylamine, and 22.6 g (0.363 mol) of potassium hydroxide (bulk industrial grade, 90.1% assay) were mixed while stirred at 20-25° C. for one hour. 40.0 g (0.363 mol) of 2-fluorotoluene was then added to the resulting slurry. The mixture was then heated to reflux (142-145° C.) for two hours and allowed to cool to about 80° C. 120 ml of water and 120 ml of toluene were added. The mixture was stirred for several minutes, and the phases were separated. The aqueous phase was extracted with 3×20 ml of toluene. The organic phases were collected and washed with 4×30 ml of water. Final organic phase weight: 206 g. Tomoxetine content: 13.25% by weight (HPLC assay). Yield: 88.4%.

Example 3

Preparation of Tomoxetine 1100 g (14.1 mol) of dimethylsulfoxide, 200 g (1.21 mol) of N-methyl-3-hydroxy-3-phenylpropylamine, and 221 g (3.63 mol) of potassium hydroxide (bulk industrial grade, 92.1% assay) were heated while stirred at 110° C. The mixture was then concentrated by vacuum distillation until about 130 g of solvent was removed. The mixture was allowed to cool to 80° C., and 400 g (3.63 mol) of 2-fluorotoluene was added. The mixture was heated to reflux (145-147° C.) for one hour and allowed to cool to about 90° C. 1000 ml of water and 1000 ml of toluene were then added. The mixture was stirred for several minutes and the phases were separated. The aqueous phase was extracted with 2×200 ml of toluene. The organic phases were collected and washed with 3×200 ml of water. Final organic phase weight: 1700 g. Tomoxetine content: 16.83% by weight (HPLC assay). Yield: 92.7%.

Example 4

Preparation of Tomoxetine 189 g (2.422 mol) of dimethylsulfoxide, 100 g (0.606 mol) of N-methyl-3-hydroxy-3-phenylpropylamine, and 188.6 g (3.028 mol) of potassium hydroxide (bulk industrial grade, 90.1% assay) were mixed while stirred and heated at 100° C. for one hour. The resulting slurry was allowed to cool to 80° C., and 200 g (1.816 mol) of 2-fluorotoluene was added. The mixture was heated to 95-100° C. for three hours and allowed to cool to about 90° C. Then 400 ml of water and 250 ml of toluene were added. The mixture was stirred for several minutes, and the phases were separated. The aqueous phase was extracted with 2×50 ml of toluene. The organic phases were collected and washed with 2×50 ml of water. Final organic phase weight: 545 g. Tomoxetine content: 26.7% by weight (HPLC assay). Yield: 94%.

Example 5

Preparation of Tomoxetine 191 g (2.448 mol) of dimethylsulfoxide, 100 g (0.606 mol) of N-methyl-3-hydroxy-3-phenylpropylamine, and 188.6 g (3.024 mol) of potassium hydroxide (bulk industrial grade, 89.9% assay) were mixed while stirred and heated at 100° C.-105° C. for one hour. The resulting slurry was allowed to cool to 80° C.-85° C., and 200 g (1.816 mol) of 2-fluorotoluene was added in one hour while the slurry was kept heated at 80° C.-85° C. The mixture was kept at 80° C.-85° C. for five hours, and 400 ml of water was added. The mixture was then stirred for several minutes, and the phases were separated. The organic phase was concentrated at reduced pressure to recover the unreacted 2-fluorotoluene. The aqueous phase was extracted with 100 ml of toluene. The organic phases were collected. Final organic phase weight: 258.5 g. Tomoxetine content: 56.6% by weight (HPLC assay). Yield: 95%.

Example 6

Tomoxetine Optical Resolution

A solution in toluene of crude racemic tomoxetine (276.13 g, 1.081 mol, by HPLC assay) prepared as described in example 1 was concentration in vacuum to remove water. The residue was taken up with 2025 ml of toluene and 26 ml of methanol. To the obtained solution 94 g (0.618 mol) of (S)-(+)-mandelic acid were added at 25° C. All solids were solubilized by heating to 65°-70° C. The crude mandelate salt was crystallized on cooling. The solid was isolated by filtration at 5°-10° C., washed with about 300 ml of toluene and dried in vacuo. Weight: 178 g. Tomoxetine content: 63.2% by weight (HPLC assay). Yield: 43.15%. Crude mandelate salt (R)-(−)-Tomoxetine enantiomeric ratio: R/S is about 95/5 (by chiral HPLC).

163 g of the obtained crude mandelate salt were re-crystallized from 489 ml of toluene and 49 ml of methanol as follows: the salt was solubilized by heating to 65°-70° C., then (R)-(−)-tomoxetine (S)-(+)-mandelate was crystallized on cooling, isolated by filtration at 5°-10° C., washed with about 2×90 ml of toluene and dried in vacuum. Weight: 153 g. Tomoxetine content: 63.97% by weight (HPLC assay). Yield: 38.7% from racemic tomoxetine. (R)-(−)-tomoxetine (atomoxetine) enantiomeric ratio: R/S>99/1 (by chiral HPLC).

Example 7

Preparation of Atomoxetine HCl 45 g (0.110 mol) of (R)-(−)-tomoxetine (S)-(+)-mandelate were mixed under stirring with 225 ml of toluene and 225 ml of water. Keeping the temperature at about 40° C. by means of gentle heating, 21 g (about 0.16 mol) of 30% aqueous sodium hydroxide were added. The phases were then separated. The organic phase was washed with 100 ml of 1% aqueous sodium hydroxide, then filtered on paper and concentrated in vacuum to give 29.67 g of an oil containing 26.8 g of tomoxetine (by HPLC assay).

23.5 g of the oil were dissolved in 211 ml of ethyl acetate under stirring then, keeping temperature between 12° C. and 18° C. by means of water-ice bath cooling; gaseous hydrogen chloride was bubbled into the solution until acid reaction of litmus paper. The hydrochloride then crystallized. The obtained suspension was stirred at about 15° C. for one hour, then the solid was collected by filtration, washed with ethyl acetate and dried in vacuo. Tomoxetine hydrochloride content: >99% by HPLC assay. Weight: 24.3 (0.0832 mol) g. Yield: 95%. Atomoxetine hydrochloride enantiomeric ratio: R/S>99/1 (by chiral HPLC).

What is claimed is:

1. A process for the preparation of tomoxetine comprising:
   (a) combining N-methyl-3-hydroxy-3-phenylpropylamine with dimethylsulfoxide (DMSO) in the presence of an alkali metal hydroxide to form a slurry;
   (b) adding 2-fluorotoluene to the slurry to obtain a reaction mixture;
   (c) heating the resultant mixture to obtain tomoxetine; and
   (d) recovering the formed tomoxetine as a racemic mixture.

2. The process of claim 1 wherein the amount of DMSO combined in step (a) is about 0.1 to about 20 mole equivalents per mole N-methyl-3-hydroxy-3-phenylpropyl-amine.

3. The process of claim 2 wherein the amount of DMSO combined in step (a) is about 3 to about 4 mole equivalents per mole N-methyl-3-hydroxy-3-phenylpropylamine.

4. The process of claim 1 wherein the alkali metal hydroxide is selected from the group consisting of potassium hydroxide, barium hydroxide, and sodium hydroxide.

5. The process of claim 4 where the alkali metal hydroxide is potassium hydroxide.

6. The process of claim 1 wherein the slurry in step (a) is heated, prior to the addition of 2-fluorotoluene in step (b), to a temperature of at least about 20° C.

7. The process of claim 6 wherein said slurry is heated to a temperature of about 80° C. to about 100° C.

8. The process of claim 1 wherein the amount of the added 2-fluorotoluene is at least about 2 molar equivalents per molar equivalent of N-methyl-3-hydroxy-3-phenyl-propylamine.

9. The process of claim 1 further comprises concentrating the slurry of step (a) prior to step (b).

10. The process of claim 1 wherein the alkali metal hydroxide is combined in step (a) in an amount of about 3 to about 5 molar equivalents per molar equivalent of the N-methyl-3-hydroxy-3-phenylpropyl amine.

11. The process of claim 1 wherein the mixture in step (c) is heated to a temperature from about 80° C. to about 145° C.

12. The process of claim 10 wherein 3 molar equivalents of said alkali metal hydroxide are used, and the mixture in step (c) is heated to a temperature of about 135° C. to about 145° C.

13. The process of claim 10 wherein 5 molar equivalents of said alkali metal hydroxide are used, and the mixture in step (c) is heated to a temperature of about 80° C. to about 100° C.

14. The process of claim 1 further comprising the step of resolving the tomoxetine racemic mixture recovered in step (d) to obtain atomoxetine or a pharmaceutically acceptable salt thereof.

15. A process for the preparation of atomoxetine or a pharmaceutically acceptable salt thereof comprising:
   (a) combining N-methyl-3-hydroxy-3-phenylpropylamine with DMSO in the presence of an alkali metal hydroxide to form a slurry;
   (b) adding 2-fluorotoluene to the slurry to obtain a reaction mixture; (c) heating the resultant mixture to obtain tomoxetine;
   (d) recovering the formed tomoxetine as a racemic mixture; and
   (e) resolving the tomoxetine racemic mixture recovered in step (d) to obtain atomoxetine or a pharmaceutically acceptable salt thereof.

16. The process of claim 15, where the pharmaceutically acceptable salt is hydrochloride.

17. A process for preparing a pharmaceutical composition comprising atomoxetine or a pharmaceutically acceptable salt thereof, which comprises:
   (a) combining N-methyl-3-hydroxy-3-phenylpropylamine with DMSO in the presence of an alkali metal hydroxide to form a slurry;
   (b) adding 2-fluorotoluene to the slurry to obtain a reaction mixture; (c) heating the resultant mixture to obtain tomoxetine;
   (d) recovering the formed tomoxetine as a racemic mixture; and
   (e) resolving the tomoxetine racemic mixture recovered in step (d) to obtain atomoxetine or a pharmaceutically acceptable salt thereof; and
   (f) bringing the atomoxetine or a pharmaceutically acceptable salt thereof formed in step (e) into contact with one or more pharmaceutically acceptable carriers or excipients.

* * * * *